(12) United States Patent
Becker et al.

(10) Patent No.: US 9,070,095 B2
(45) Date of Patent: Jun. 30, 2015

(54) ENSURING REFERENTIAL INTEGRITY OF MEDICAL IMAGE DATA

(75) Inventors: Detlef Becker, Möhrendorf (DE); Karlheinz Dorn, Kalchreuth (DE); Andrew John Hewett, Erlangen (DE); Armin Michel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1559 days.

(21) Appl. No.: 12/078,553

(22) Filed: Apr. 1, 2008

(65) Prior Publication Data

US 2009/0248440 A1    Oct. 1, 2009

(51) Int. Cl.
| G06F 19/00 | (2011.01) |
| G06Q 10/06 | (2012.01) |
| G06Q 50/22 | (2012.01) |

(52) U.S. Cl.
CPC ............... *G06Q 10/06* (2013.01); *G06Q 50/22* (2013.01)

(58) Field of Classification Search
USPC ............. 707/1, 9, 100; 717/102; 705/1, 7, 30, 705/41, 2-3; 709/217, 223, 219; 382/128, 382/131
See application file for complete search history.

(56) References Cited

U.S. PATENT DOCUMENTS

| 6,629,081 | B1 * | 9/2003 | Cornelius et al. ............... 705/30 |
| 2001/0056362 | A1 * | 12/2001 | Hanagan et al. ................... 705/7 |
| 2002/0052862 | A1 * | 5/2002 | Scott et al. ......................... 707/1 |
| 2002/0078432 | A1 * | 6/2002 | Charisius et al. ............. 717/102 |
| 2002/0138582 | A1 * | 9/2002 | Chandra et al. ............... 709/206 |
| 2003/0005464 | A1 * | 1/2003 | Gropper et al. ............... 725/115 |
| 2003/0105805 | A1 * | 6/2003 | Jorgenson ...................... 709/203 |
| 2003/0195765 | A1 * | 10/2003 | Sehgal et al. ...................... 705/1 |
| 2004/0139018 | A1 * | 7/2004 | Anderson et al. ............... 705/41 |
| 2005/0108365 | A1 * | 5/2005 | Becker et al. .................. 709/219 |
| 2005/0246629 | A1 * | 11/2005 | Hu .................................. 715/513 |
| 2005/0257136 | A1 * | 11/2005 | Charisius et al. ............. 715/511 |
| 2006/0143041 | A1 * | 6/2006 | Tipirneni ........................... 705/2 |
| 2006/0173985 | A1 * | 8/2006 | Moore .......................... 709/223 |
| 2007/0027630 | A1 * | 2/2007 | Sanchez .......................... 702/19 |
| 2007/0112714 | A1 * | 5/2007 | Fairweather .................... 706/46 |
| 2007/0118540 | A1 * | 5/2007 | Guo .............................. 707/100 |
| 2007/0156696 | A1 * | 7/2007 | Lim .................................. 707/9 |
| 2007/0162907 | A1 * | 7/2007 | Herlocker et al. ............. 718/100 |
| 2007/0282581 | A1 * | 12/2007 | Mangino et al. .................. 703/6 |
| 2007/0288212 | A1 * | 12/2007 | Messmer et al. .................. 703/6 |
| 2008/0077001 | A1 * | 3/2008 | Ruscio et al. .................. 600/407 |
| 2009/0164474 | A1 * | 6/2009 | Noumeir ......................... 707/10 |

OTHER PUBLICATIONS

Digital Imaging and Communications in Medicine (DICOM), Part 3: Information Object Definitions National Electrical Manunfacturers Association, 1300 N, 17th Street; 2008; pp. 1-1097.

* cited by examiner

*Primary Examiner* — Michelle L Le
(74) *Attorney, Agent, or Firm* — Harness, Dickey & Pierce

(57) ABSTRACT

A method, a system and a computer program product are disclosed for providing information concerning scheduled procedure steps and/or information concerning performed procedure steps within a taskflow which includes a plurality of tasks for processing medical image data. Each taskflow is associated with a taskflow specific context folder. In at least one embodiment, a publisher task is adapted to select selected data out of the medical image data. For these selected data, meta-information is updated by incorporating additional information concerning scheduled procedure steps and performed procedure steps. This is done by maintaining referential integrity between image data, scheduled procedure steps and performed procedure steps.

13 Claims, 2 Drawing Sheets

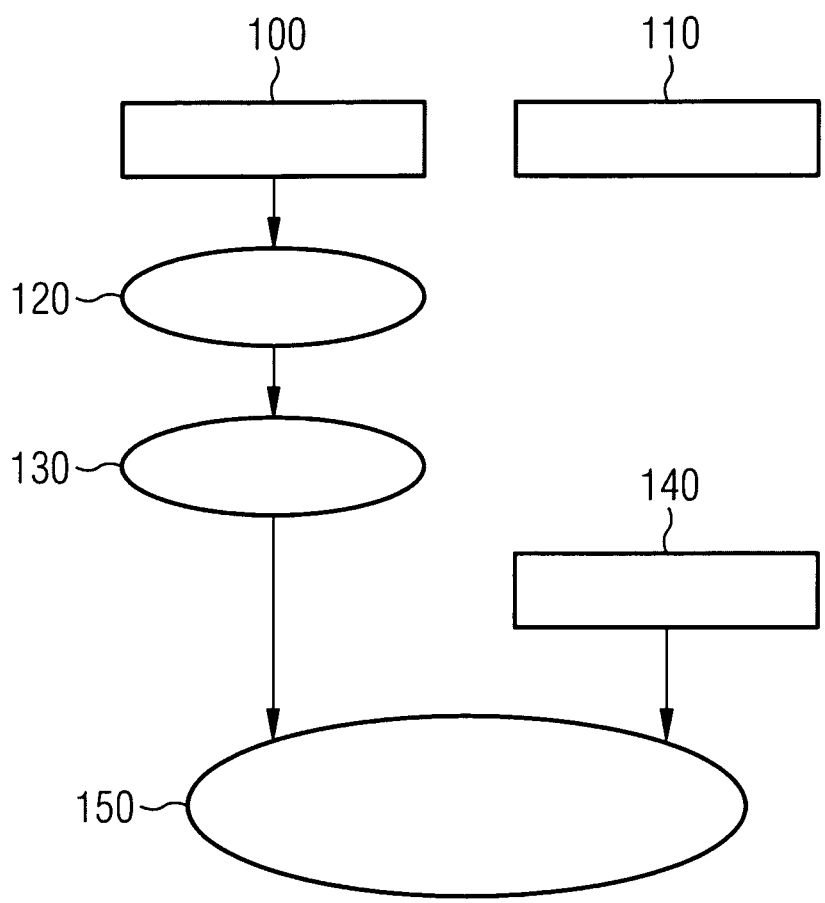

ENSURING REFERENTIAL INTEGRITY OF MEDICAL IMAGE DATA

FIELD

Embodiments of the present invention generally relate to ensuring referential integrity of medical image data, wherein medical image data are processed in a taskflow, including several tasks. The tasks are adapted to process image data.

BACKGROUND

Nowadays, a lot of clinical systems are based on the DICOM standard. The DICOM standard provides several procedure steps for processing medical data. Particularly, DICOM standard part 3, section 7, point 3.1 defines procedure steps and classifies two types of procedure steps, namely "scheduled procedure steps" and "performed procedure steps". The scheduled procedure steps refer to those actions for steps which are planned or scheduled, respectively, whereas the performed procedure steps refer to those actions or steps, having actually been performed. The scheduled procedure steps might differ from the performed procedure steps, particularly in case of emergency situation, which generally might lead to a change of the scheduled taskflow.

Thus, important information is to be seen in what kind of procedure steps have been performed on the data objects and what kind of procedure steps only have been scheduled for these data objects. This information has to be consistent across all created data. With other words referential integrity must be maintained.

The applicant has developed a platform, the syngoII platform for running a plurality of applications. The applications, also named as tasks in this respect, are independently developed by independent developer groups. Up to now it was necessary that each of these applications (tasks) itself dealt separately with maintaining referential integrity. Thus, in the state of the art this was very error-prone and time-consuming procedure.

SUMMARY

Therefore, the inventors recognized that a need exists for a simplification of maintaining referential integrity. Further, they recognized that a need exists for eliminating this responsibility (maintaining referential integrity) for each and every application.

The method according to at least one embodiment of the present invention allows for providing information concerning scheduled procedure steps and/or information concerning performed procedure steps within a taskflow out of a plurality of different taskflows. A taskflow is constituted by a plurality of tasks. A task typically is an application for processing medical image data, such as for example a diagnostic reporting application, a post processing application or other tasks, to be performed on the medical image data or on data, associated with the medical image data.

Each taskflow has a private memory for storing taskflow specific data, named contest folder. With other words, the context folder is adapted to store taskflow internal data or taskflow private data, which in general might not be accessible from outside the specific taskflow.

According to one aspect of at least one embodiment of the invention, the method comprises:

selecting data out of the medical image data, stored in the context folder, wherein the data is to be made available to external entities;

updating meta-information for the selected data by means of providing information concerning scheduled procedure steps and/or providing information concerning performed procedure steps within the taskflow; and maintaining referential integrity between selected data, scheduled procedure steps and performed procedure steps by means of a publisher task, being independent of the tasks of the taskflow.

Hereafter, provided is a short explanation and definition of terms used in this disclosure.

"Scheduled procedure steps" include steps being planned, intended but not yet or not at all performed, whereas "performed procedure steps" are those steps, which actually have been carried out or performed, independent of the fact whether or not they have been scheduled.

A "taskflow" is a subset of departmental workflow or the workflow of a clinic. A taskflow typically includes a plurality of tasks. The tasks might be implemented by applications. Thus, a taskflow includes a sequence of separate tasks for processing medical data.

In addition to the term "taskflow" there does also exist a "workflow". A workflow is a superordinate structure and characterizes a (typically) planned, repeatable and documentable process in the clinical/radiological environment. It can be broken down in further units of work, such as tasks and steps, as mentioned above. A result or outcome of a workflow is usually represented by one or more diagnostic reports and/or patient treatments. A complete workflow often contains also tasks which are not performed within a scope of the described system. In this case, these tasks are characterized as being only scheduled procedure steps.

A taskflow is defined by a taskflow template, in which the orchestration of clinical tasks is described. It typically includes a mostly sequentially ordered list of tasks (user-interactive as well as automatically), steps and tools which are depending of the surrounding workflow's intent. The taskflow template, as mentioned above, specifies the content of a taskflow. It describes the technical tasks, the control and data flow, the association of technical tasks to clinical tasks and the grouping of clinical tasks to work items. A work item is a combination of separate tasks such that several tasks might be combined to form a work item.

The term "medical image data" is to be construed as medical data in general, which according to one aspect of at least one embodiment of the invention might be image data, such as radiology image data or a data based on another modality. According to another aspect of at least one embodiment of the invention these medical data also might be textual data or other data, associated with medical and/or clinical questions, such as financial information or administrative information or meta-data.

The term "meta-information" is to be understood as additional information, being associated with the medical image data, such as associated data concerning general aspects of the medical image data. According to one aspect of at least one embodiment of the invention the medical data is held in a specific format for processing medical image data, like the DICOM format. In this case the meta-information is a DICOM header.

"Maintaining referential integrity" includes automatically maintaining consistency between the data. Particularly, selected data, scheduled procedure steps and performed procedure steps are to be held consistent either within the taskflow or also across several taskflows. The responsibility for ensuring referential integrity according to the invention is moved away from the single task (application) and is moved to a separate central task, the publisher task. The referential integrity is maintained by up dating cross-references to data objects, wherein the data objects are referring to scheduled procedure steps and planned procedure steps.

According to the DICOM standard, newly created medical image data which is transmitted to other devices or entities must be cross-referenced with the data objects representing the scheduled procedure steps and with the data object representing the performed procedure steps. These cross-references must be consistent across all created data. This is meant with the wording "referential integrity must be maintained".

According to another aspect of at least one embodiment of the present invention selecting is based on global and/or taskflow specific rules. This is an advantageous aspect, as each taskflow might have its own specific rules. Additionally, also common rules might be definable, which relate to several taskflows.

According to another aspect of at least one embodiment of the invention, the step of updating is carried out at pre-definable time points within the taskflow or according to pre-definable rules. In this respect it should be noted that these rules are time related rules, whereas the rules mentioned above for selecting the data, which should be made available for external entities are selection rules. Either the time related rules and the selection related rules might be held in one data structure or in a common memory section. Either the selection rules as well as the time related rules are dynamically adaptable to the specific clinical situation. This leads to the advantage that the method according to at least one embodiment of the invention is flexible and easily adaptable to different situations.

According to another aspect of at least one embodiment of the present invention the selected data is stored in a short time storage. The term "selected data" refers to those data for which it is defined that they should be made available to external entities, such as other taskflows, external devices, other applications, other networks etc. Relating to the memories or repositories there do exist two categories of memories: The first category refers to a taskflow private storage, which is associated with each taskflow. This is named the context folder. And the second category refers to the short term storage (often also abbreviated as "STS"), which holds publically available data or data visible to all taskflows and to external devices.

According to another aspect of at least one embodiment of the invention, the selected data is checked before or after being stored. This has the advantage that the quality of the method according to at least one embodiment of the invention might be improved.

According to a further aspect of at least one embodiment of the invention the method comprises:
 making available the information concerning scheduled procedure steps and/or the information concerning performed procedure steps to an initializer, which is adapted to start the taskflow.

The term "initializer" refers to a superordinate entity, which is adapted to start the taskflow. In a specific platform of the applicant, called "syngoII", the initializer is a so-called workflow framework which provides the taskflow with the scheduled procedure steps and associates a prototype for performed procedure steps with each work item. The prototype for the performed procedure steps contains all information known when the taskflow starts (i.e. all request information and cross-references to the scheduled procedure steps).

According to another aspect of at least one embodiment of the invention separate instances of the publisher task are generated. With this feature concerning multiple instances, an increased responsiveness could be gained. However, this advantage is also associated with the expense of increased use of system resources.

Alternatively, in at least one embodiment, a single instance of the publisher task may be used for each taskflow in order to save system resources. A common pattern is to have a 1:1-relationship between data publisher task and work item. A single instance requires minimal system resources but can have a slower response. Another common pattern is to have a 1:n-relationship between the publisher task and a work item, which—as mentioned above—includes a combination of tasks.

According to another aspect of at least one embodiment of the invention all the steps or specific, selected steps are carried out automatically. Preferably, the updating of meta-information and the maintaining referential integrity are steps, which usually are carried out automatically. Automatically refers to, in this respect, a process without user interaction. Concerning the step of selecting data out of the medical image data which should be made available to external entities there do exist several possibilities. It also is possible, in at least one embodiment, to execute the selection of a data as automatic step. Further, it is also possible, in at least one embodiment, to perform this step half-automated, i.e. with user interaction. For example the user could be provided with a list, comprising a proposal for data to be published (to be made available to external entities). Then, the user might identify those data categories as proposed which he wants to make publically available.

According to a further aspect of at least one embodiment of the present invention the taskflow is controlled by a workflow engine, being a superordinate entity for the taskflow and wherein the workflow engine automatically creates the publisher task. Thus, all tasks within the taskflow and the flow of data over ports, wherein the ports are interfaces between different tasks of a taskflow in order to pass data between sequential tasks, are controlled by a workflow engine. This workflow engine is also adapted to create a specialized task, namely the data publisher task. The data publisher task is automatically invoked by the workflow engine. The publisher task can be configured to be invoked at the end of any work item. Alternatively it can be adapted to be invoked at other time points, particularly at the end of any task. The publisher task has access to the scheduled procedure steps and the prototype performed procedure steps information and to all data created by the tasks.

Additionally, the publisher task has the job to transform taskflow internal data into taskflow external data. Taskflow internal data is stored in the taskflow specific context folder, whereas taskflow external data is available publically and thus it is available also for external entities. Data generated by the tasks within a taskflow must be published from the context folder to the short term storage. This data can be published at the end of each work item or at the latest at the end of the final work item. Typically, only a subset of data created by the task within the taskflow will be published to the short term storage. Accordingly, some of the created data will be temporary and will never be communicated to another device (e.g. never sent to an archive system). For this temporary data it is unnecessary to maintain cross-references.

Further, in at least one embodiment, the temporary data is not referenced by other objects (e.g. a performed procedure step should not reference temporary data). The decision about which data is intended to be externalized (or published) is typically not made by the application creating the data. Particularly, within a workflow of independent connected tasks an individual task does not know how the output data it generates will be used as input data by subsequent tasks within the workflow.

According to one aspect of at least one embodiment of the invention, this decision as mentioned above (which data are intended to be externalized) is made under the responsibility of a specialized application, namely of the publisher task. This leads to a separation of concerns and to an encapsulation of a business logic. With other words cross-referencing takes only place when needed. Cross-referencing is done at appropriate points within the workflow. For example a temporary data will not be cross-referenced according to at least one embodiment of the invention.

An important aspect of at least one embodiment of the present invention is to be seen in the fact that only selected data, which is data intended to be accessible to external devices, entities etc., are updated. Further, only selected data is referenced within the scheduled/performed procedure step. On the one hand this leads to an increased performance and on the other hand it ensures referential integrity.

According to another aspect of at least one embodiment of the present invention, there are provided global and workflow specific rules to determine any actions to be performed on the selected data (published data) (e.g. send the data to remote devices, write to DVD, print).

Until now at least one embodiment of the present invention has been described in relation to the method. Any aspects, features or advantages mentioned in this respect might also be applied to a system according to at least one embodiment of the invention, and also to the computer program product according to at least one embodiment of the invention. The system and the product of at least one embodiment might also be adapted to incorporate features, having been mentioned with respect to the description of the method according to at least one embodiment of the invention. Any functional feature refers to an apparatus feature, having the respective functionality. For example the step of "providing specific" rules may refer to a "rule database for storing these specific rules" in at least one embodiment. Further, the step of "storing" may refer to a specific "storage" for carrying out the storing of data in at least one embodiment.

According to another aspect of at least one embodiment of the invention, there is provided a system for providing information concerning scheduled procedure steps and/or information concerning performed procedure steps within a taskflow. Each taskflow is associated with a taskflow specific context folder for storing taskflow specific data. The system comprising:

a selection module for selecting data out of the medical image data, stored in the context folder, wherein the data is to be made available to external entities;

an updating module for updating meta-information for the selected data by means of providing information concerning scheduled procedure steps and/or concerning performed procedure steps within the taskflow; and an integrity module for maintaining referential integrity between selected data, scheduled procedure steps and performed procedure steps by means of a publisher module, being separate from the tasks of the taskflow.

The integrity module is adapted to maintain referential integrity only between the relevant (published) medical image data, i.e. only for the selected data. Normally, the selected data are a subset of the medical image data, which are to be made available to external entities or devices or external taskflows.

According to another aspect of at least one embodiment of the invention, the system includes a workflow engine for controlling the tasks of the taskflow and for generating the selection module, the updating module and the integrity module.

According to further aspect of the present system according to at least one embodiment of the invention is to provide interfaces. Typically, the system has at least one interface to an information system, like a radiology information system (shortly: RIS). The RIS provides information relating to the scheduled procedure steps. The system according to at least one embodiment of the invention updates the meta-information for the relevant (the selected) data with the scheduled procedure steps. After completion of several tasks or of a work item the system also updates the meta-information with information relating to the actually performed procedure steps for the selected data. This may be done by adding to the meta-information cross-references to objects, relating to scheduled procedure steps and/or performed procedure steps. Again, it has to be repeated that only those data are cross-referenced which have been selected. After completion of the taskflow or of a part of the taskflow the information concerning the scheduled procedure steps as well as the performed procedure steps are being made available to the radiology information system.

Another interface of the system according to at least one embodiment of the invention is a controlling interface. In this example of at least one embodiment of the invention, a workflow engine is not part of the system, but is provided as separate module, having an interface to the system, described above. Alternatively, the workflow engine could also be part of the system.

Another aspect of at least one embodiment of the invention is to be seen in a computer program being loadable in a memory of a computer, wherein the computer program is adapted to carry out the steps of the method as mentioned above.

BRIEF DESCRIPTION OF THE DRAWINGS

FIG. 2 is a flowchart for a possible sequence of steps according to one embodiment of the invention.

DETAILED DESCRIPTION

Figure 1:
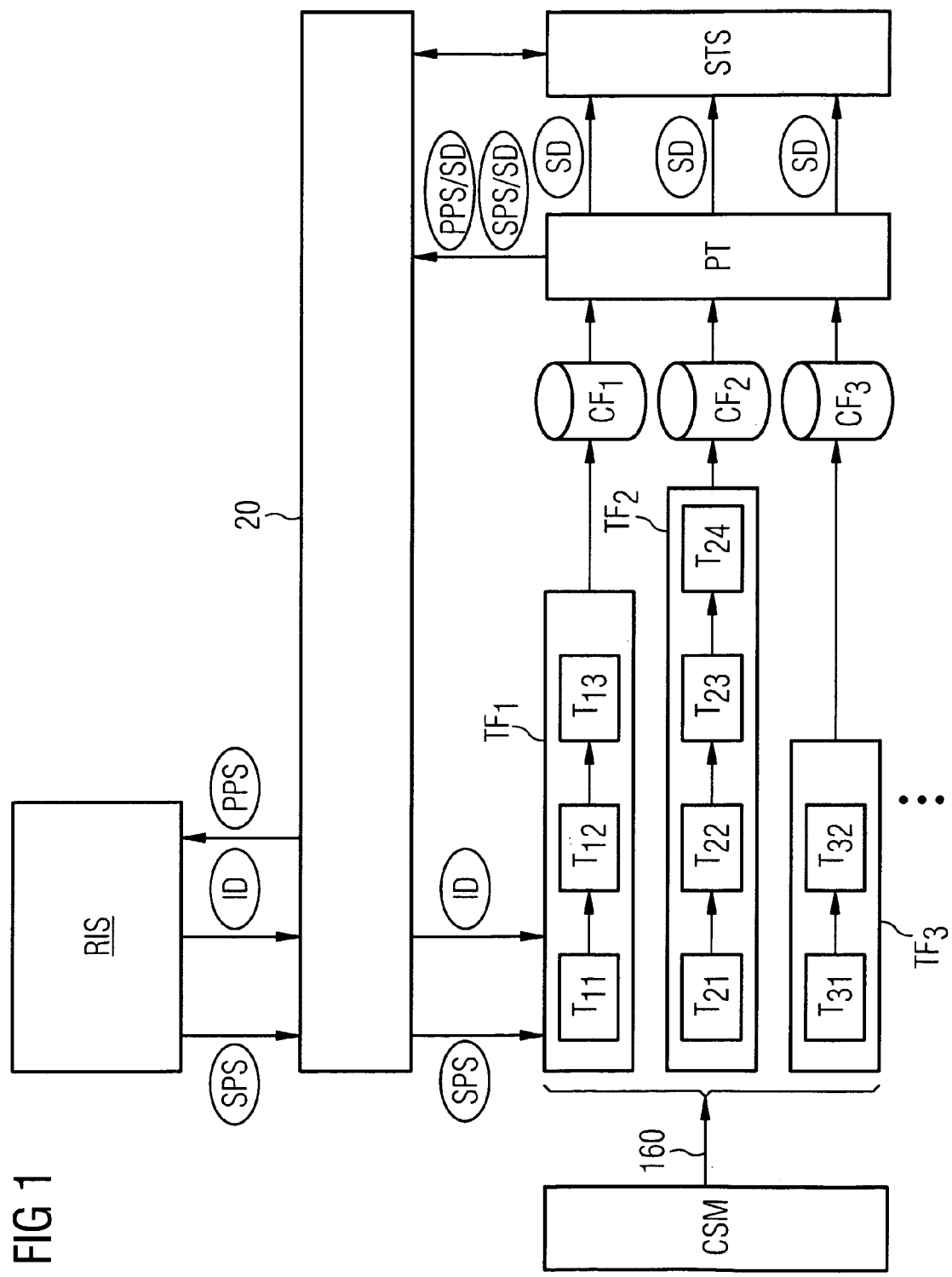
FIG. 1 is a schematic representation of several modules in accordance with an embodiment of the invention.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Embodiments of a method for providing information concerning scheduled procedure steps SPS and/or information concerning performed procedure steps PPS and for maintaining referential integrity are described hereinafter. In the following description, specific details are given to provide a thorough understanding of example embodiments of the invention. One skilled in the relevant art will recognize, however, that aspects of embodiments of the invention can be practiced without one or more of the specific details, or with other methods, modules, entities etc. In other instances, well-known structures, computer related functions or operations are not shown or described in detail, as they will be understood by those skilled in the art.

Further, the method of an example embodiment is described with respect to medical image data. However, it is apparent that also other categories or another kind of data, for example like textual data etc., might also be applied and processed, respectively.

References throughout this specification to "one/an embodiment" means that a particular feature, structure or characteristic described in connection with the embodiment is included in at least one embodiment of the present invention. Thus, the appearances of the phrases "according to one embodiment" or the like in various places throughout this specification are not necessarily all referring to the same embodiment. Furthermore, the particular features, structures or characteristics may be combined in any suitable manner in one or more embodiments.

According to one embodiment of the present invention a method for providing information concerning scheduled procedure steps SPS and/or information concerning performed procedure steps PPS within a taskflow TF out of a plurality of different taskflows TF is provided. The taskflow TF includes a plurality of tasks T for handling, storing, processing or referring to medical image data ID. One task T is an activity, usually represented by an application, on the image data ID.

With respect to FIG. 1 it can be seen that each taskflow TF has its own taskflow private or taskflow specific context folder CF. Each of the context folders CF is adapted for storing taskflow specific data.

The method according to at least one embodiment of the invention is a computer implemented method, which might be used in any PC, network, notebook or other computer programmable devices/modules and/or apparatuses. Also, the method according to at least one embodiment of the invention might be used in a medical or clinical system, such as the so-called syngoII platform, provided by the applicant.

Applications within syngoII are organized as tasks T within the above mentioned taskflow TF which are connected by ports over which data is passed. An output port of one task T is connected to an input port of another task T. Taskflows TF are typically constructed by selecting tasks T and connecting them together via ports. Furthermore, tasks T are grouped into work items where each work item represents a unit of work to be preformed by a single person (clinical staff, physicians etc.).

In view of FIG. 1 it can be seen that the system further includes a memory, a so-called short term storage memory STS. This is a repository for storing those data, which should be made available for other instances. With other words only publically available data or published data visible to all taskflows TF and to all external devices are to be stored in this short term storage STS.

Tasks T within the taskflow TF and flow of data over ports are controlled by a workflow engine CSM.

As FIG. 1 is a combination of structural elements and of functional elements it can be seen that in step 160 the workflow engine CSM is adapted to control the taskflows TF. In FIG. 1 it is shown that the first taskflow $TF_1$ consists of three tasks $T_{11}$, $T_{12}$ and $T_{13}$, whereas the second taskflow $TF_2$ comprises four tasks, namely $T_{21}$, $T_{22}$, $T_{23}$ and $T_{24}$ and wherein the third taskflow $TF_3$ comprises only two tasks T, namely $T_{31}$, and $T_{32}$. The three taskflows $TF_1$, $TF_2$ and $TF_3$ depicted in FIG. 1 have its private context folders $CF_1$, $CF_2$ and $CF_3$.

According to at least one embodiment of the invention there is created a specialized task, namely the publisher task PT. The publisher task PT might automatically be invoked by the workflow engine CSM. The publisher task PT can be configured to be invoked at different points in time. For example the publisher task PT might be configured to be invoked at the end of any work item. Alternatively, the publisher task PT might be initiated after each task T or after a selection of tasks T. For one skilled in the relevant art it will be recognized that the publisher task PT also might be enabled or activated according to pre-definable rules.

According to one embodiment of the present invention, the system interacts with a framework 20. This workflow framework is a computer implemented entity which starts the taskflow TF. Furthermore, the workflow framework provides the taskflow TF with the scheduled procedure steps SPS and associates a prototype of performed procedure steps PPS with each work item. Typically, the scheduled procedure steps SPS are provided by a information system, like a radiology information system RIS. In this sense the framework 20 interacts as interface between the RIS and the system according to the invention, comprising the taskflows TF, to be controlled by the workflow engine CSM, the context folders CF, the publisher task PT and the short term storage repository STS.

From the radiology information system RIS and/or from the framework 20 there are provided the scheduled procedure steps SPS and the image data ID. After processing the image data ID in one or several taskflows TF according to the scheduled procedure steps SPS or according to modified procedure steps (wherein the modification might be due to an emergency case and possibly leads to another sequence of tasks or to others tasks T), the publisher task PT determines which of the image data, stored in the several context folders CF are to be made available to other entities. The publisher task PT then selects selected data SD out of the image data ID. In this connection the publisher task PT is adapted to select a subset (selected data SD) out of the set of image data ID.

In a further step of the present invention according to an embodiment of the invention the publisher task PT then combines at least one data object, relating to procedure steps, namely for example to the scheduled procedure steps SPS and/or to the performed procedure steps PPS, with to the selected data SD. The selected data SD are being made available to external entities and are to be stored in the short term storage STS.

Finally, the publisher task PT adds a further object to the selected data SD. According to one embodiment of the invention the further object is to be seen in the scheduled procedure steps SPS. In another embodiment of the invention the further object is to be seen in the performed procedure steps PPS. Whereas in a third embodiment of the invention a further object is to be seen in a combination of the scheduled procedure steps SPS and in the performed procedure steps PPS. This addition of the further object to the selected data SD should be depicted in FIG. 1 with the denotation "PPS/SD" and "SPS/SD" with respect to vertical arrow, starting from the publisher task PT and aiming at the framework 20.

FIG. 2 describes a typical workflow of the present invention according to one embodiment. In step 100 there are provided the image data ID. In step 110 there are provided the scheduled procedure steps SPS. These provisions might be done by the radiology information system RIS and/or by the framework 20.

After this, in step 120 the selected data SD are selected out of the image data ID. Usually, the selected data SD are a subset of the image data ID. This leads to performance improvements, since only a smaller set of data might to be processed further. The additional objects concerning the procedure steps, scheduled procedure steps SPS and performed procedure steps PPS are only to be added for the selected data SD.

In step 130 meta-information for the selected data SD are updated. More specifically the DICOM header is updated with the scheduled procedure steps SPS. This is done by adding an object referring to information concerning the scheduled procedure steps SPS to the DICOM header.

In step 140 there are provided the performed procedure steps PPS. Step 140 can only be carried out after processing the image data ID by means of the taskflows TF. The exact timepoint for carrying out step 140 is adaptable according to pre-definable rules. Further, step 110 might be carried out independently of step 140.

After provision of the performed procedure steps PPS the meta-information, particularly the DICOM header, once more might be updated with an additional data object. This additional data object concerns information with respect to the performed procedure steps PPS, which actually have taken place by means of the tasks T in the taskflows TF. According to one embodiment of the present invention the DICOM header is modified such as it includes further at least one data object concerning information with respect to the scheduled procedure steps SPS and/or to the performed procedure steps PPS. According to one embodiment of the invention the DICOM header includes two separate data objects for the information concerning the scheduled procedure steps SPS and one for the performed procedure steps PPS. Alternatively, it is also possible to only incorporate one additional data object, in which this information, mentioned above, is included. In this embodiment one data object, to be included in the DICOM header comprises the performed procedure steps PPS and the scheduled procedure steps SPS for the selected data SD.

It is to be understood that during the whole method according to at least one embodiment of the invention a referential integrity is maintained. Particularly there is maintained a data consistency between selected data SD, scheduled procedure steps SPS and performed procedure steps PPS by means of the publisher task PT. Regularly, the referential integrity is maintained by way of cross-references to the respective data.

The publisher task PT has the following responsibilities.

Firstly, the global and taskflow specific configuration is to be evaluated in order to determine which image data ID should be published as selected data SD.

Secondly, the meta-information, particularly the DICOM header for all selected data SD is updated with:
a) the identity of performed procedure steps PPS associated with the current work item (image cross-reference to performed procedure steps PPS) and
b) the identity of scheduled procedure steps SPS associated with the taskflow T (image cross reference to scheduled procedure steps SPS).

Thirdly, the performed procedure steps PPS associated with the current work item are to be updated with the identity of all selected data SD which was created during this work item (performed procedure steps PPS cross-reference to image data ID).

Fourthly, the selected data SD to be published into the short term storage STS should be checked. This is to reduce errors or faults.

Fifthly, any subsequent actions configured to be performed on the selected data SD might be invoked automatically, half-automatically or manually. Such actions might be "sending to remote instance", "write to DVD", "print to film or paper".

Sixthly, the updated performed procedure steps PPS are to be made available to an instance which started the taskflow TF. This instance is called an initializer.

Throughout the above mentioned detailed description the term "scheduled procedure steps SPS" and "performed procedure steps PPS" might be implemented, in at least one embodiment, by at least one data object. Accordingly, there might be an SPS-object and an PPS-object. Alternatively, it is also possible, in at least one embodiment, to combine this information in one single data object, as mentioned above. It is possible that the data object itself includes the information concerning the procedure steps. As an equivalent solution it might be that the data object, in at least one embodiment, includes the reference to this information. The information might be stored at a separate instance in the system.

The transfer of information of information concerning the procedure steps between the radiology information system RIS, the framework 20 and the taskflow system according to at least one embodiment of the invention might be implemented by means of messages. Thus, there is a workflow framework which interfaces with the radiology information system RIS to receive SPS messages and subsequently determines which taskflow template to use. The data publisher task PT passes the PPS-information (PPS-message) to the workflow framework which analyzed the contained information and sends the PPS-message and/or the SPS-message back to the radiology information system RIS.

For performance reasons and according to an embodiment of the present invention the PPS-information should not reference temporary data which will never be made available to external devices (for example the STS). This feature enables to eliminate inefficiencies in the workflow and delays in distribution of diagnostic reports to referring physicians, known in the state of the art systems. Typically, a radiology information system RIS receives a PPS which references 1000 images and waits until all images have been transferred to the picture archiving and communication system (PACS-image archive) before scheduling diagnostic reporting. If 100 of the images referenced by the PPS are temporary, they will never arrive at the PACS and the RIS will wait for a time-out or user intervention before scheduling diagnostic reporting. This time-out or delay situation might be avoided according to at least one embodiment of the invention.

The above description of illustrated embodiments of the invention is not intended to be exhaustive or to limit the invention to precise forms disclosed. While specific embodiments of, and examples for, embodiments of the invention are described herein for illustrative purposes various equivalent modifications are possible within the scope of the invention and can be made without a deviating from the spirit and scope of the invention.

For instance, the description is based on the DICOM format. Alternatively, another medical format might also be used for the method and system according to at least one embodiment of the invention.

Further, the method might be implemented in software, in coded form. Alternatively, it is possible to implement the method according to at least one embodiment of the invention in hardware or hardware modules. The hardware modules are then adapted to perform the functionality of the steps of the method. Furthermore, it is possible to have a combination of hardware and software modules.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

These and other modifications can be made to the invention with regard of the above detailed description. The terms used in the following claims should not be construed to limit the invention to the specific embodiments disclosed in the specification and the claims. Rather, the scope of the invention is to be determined entirely by the following claims, which are to be construed in accordance with established doctrines of claim interpretation.

What is claimed is:

1. A method for managing information concerning at least one of scheduled procedure steps and performed procedure steps within a taskflow, the method comprising:

generating, by a computer processor, a workflow engine configured to generate and control a plurality of different taskflows including the taskflow, the plurality of different taskflows being associated with one or more medical procedures, the taskflow including a plurality of tasks to process medical image data, each of the plurality of different taskflows being associated with a private context folder to store taskflow specific data, the private context folder not being accessible by external entities; and generating, by the computer processor, a publisher task for,
  selecting data from the medical image data, stored in the private context folder,
  providing the selected data to the external entities using a short term allocation of a non-transitory computer readable memory,
  generating the information concerning at least one of the scheduled procedure steps and the performed procedure steps within the taskflow, the scheduled procedure steps being scheduled medical steps that are to be implemented, the performed procedure steps being medical steps the implementation of which are completed, updating meta-information for the selected data with the information, and maintaining referential integrity between the selected data, the scheduled procedure steps and the performed procedure steps, wherein the updating updates the meta data information by adding an object to the meta-information of the selected data, the object referring to the information, the meta-data information is a Digital Imaging and Communication in Medicine (DICOM) header information of the selected data, and the publisher task is associated with the workflow engine and is independent from the plurality of tasks of the taskflow.

2. The method according to claim 1, wherein the data is medical data in a DICOM format.

3. The method according to claim 1, wherein the selecting is based on at least one of global and taskflow specific rules.

4. The method according to claim 1, wherein the updating is carried out at least one of at pre-definable timepoints within the taskflow and according to pre-definable rules.

5. The method according to claim 1, wherein the selected data is stored in a short time storage.

6. The method according to claim 1, wherein the selected data is checked at least one of before and after being stored.

7. The method according to claim 1, further comprising:
providing the information concerning at least one of the scheduled procedure steps and the information concerning performed procedure steps to an initializer configured to start the taskflow.

8. The method according to claim 1, wherein separate instances of the publisher task are generated.

9. The method according to claim 1, wherein a single instance of the publisher task is used for each taskflow.

10. The method according to claim 1, wherein at least one of the selecting, updating and maintaining is carried out automatically.

11. A system configured to manage information concerning at least one of scheduled procedure steps and performed procedure steps within a taskflow, the system comprising:
at least one computer processor configured to,
generate a workflow engine to generate and control a plurality of different taskflows including the taskflow, the plurality of different taskflows being associated with one or more medical procedures, the taskflow including a plurality of tasks to process medical image data, each taskflow being associated with a private context folder to store taskflow specific data, the private context folder not being accessible by external entities; and
generate a publisher task, the publisher task being associated with the workflow engine and independent from the plurality of tasks of the taskflow, the publisher task being configured to,
select data from the medical image data, stored in the private context folder,
provide the selected data to the external entities using a short term allocation of a non-transitory computer readable memory,
generate the information concerning at least one of the scheduled procedure steps and the performed procedure steps, the scheduled procedure steps being scheduled medical steps that are to be implemented, the performed procedure steps being medical steps the implementation of which are completed,
update meta-information for the selected data with the information, and
maintain referential integrity between the selected data, the scheduled procedure steps and the performed procedure steps, wherein
the publisher task is configured to update the meta-data information by adding an object to the meta-information of the selected data, the object referring to the information, and
the meta-data information is a Digital Imaging and Communication in Medicine (DICOM) header information of the selected data.

12. The method according to claim 7, wherein at least one of the selecting, updating, maintaining and providing is carried out automatically.

13. A non-transitory computer readable medium including program segments for, when executed on a computer device, causing the computer device to:
generate a workflow engine to generate and control a plurality of different taskflows, the plurality of different taskflows being associated with one or more medical procedures, at least one of the plurality of different taskflows including a plurality of tasks to process medical image data, each of the plurality of different taskflows being associated with a private context folder to store taskflow specific data, the private context folder not being accessible by external entities; and
generate a publisher task for,
selecting data from the medical image data, stored in the private context folder,
providing the selected data to the external entities using a short term allocation of a non-transitory computer readable memory,
generating information concerning at least one of scheduled procedure steps and performed procedure within the at least one of the plurality of different taskflows, the scheduled procedure steps being scheduled medical steps that are to be implemented, the performed procedure steps being medical steps the implementation of which are completed,
updating meta-information for the selected data with the information, and
maintaining referential integrity between the selected data, the scheduled procedure steps and the performed procedure steps, wherein
the publisher task updates the meta-data information by adding an object to the meta-information of the selected data, the object referring to the information,
the meta-data information is a Digital Imaging and Communication in Medicine (DICOM) header information of the selected data, and
the publisher task is associated with the workflow engine and is independent from the plurality of tasks.

* * * * *